United States Patent [19]

deNeui

[11] B 4,001,072
[45] Jan. 4, 1977

[54] APPLICATOR FOR PRESSURE-SENSITIVE ADHESIVE FASTENERS

[75] Inventor: Richard P. deNeui, Lake Elmoin, Minn.

[73] Assignee: Minnesota Mining and Manufacturing Company, St. Paul, Minn.

[22] Filed: Sept. 13, 1972

[21] Appl. No.: 288,757

[44] Published under the second Trial Voluntary Protest Program on March 30, 1976 as document No. B 288,757.

[52] U.S. Cl. .......................... 156/461; 128/290 R; 156/66; 156/201; 156/204; 156/289; 156/518; 156/520

[51] Int. Cl.$^2$ ..................... B32B 31/00; B31F 1/00

[58] Field of Search ............ 156/66, 200, 201, 202, 156/204, 250, 264, 265, 461, 463, 467, 519, 520, 521, 552, 289; 161/413; 24/67 R, 67 AR, DIG. 11; 83/327, 328, 341, 509–511, 100, 592; 128/287, 290 R

[56] References Cited

UNITED STATES PATENTS

| | | | |
|---|---|---|---|
| 1,989,012 | 1/1935 | Kalko | 83/328 |
| 2,133,341 | 10/1938 | Bronander | 156/520 X |
| 2,379,859 | 7/1945 | Barnard | 83/592 X |
| 2,642,116 | 6/1953 | Fisher et al. | 156/520 X |
| 2,929,437 | 3/1960 | Stevens | 156/467 |
| 2,934,117 | 4/1960 | Urschel et al. | 83/327 X |
| 3,257,678 | 6/1966 | Batchelder et al. | 24/DIG. 11 |
| 3,322,600 | 5/1967 | Harrison et al. | 156/461 |
| 3,334,784 | 8/1967 | Morrison | 221/7 |
| 3,472,724 | 10/1969 | Casey | 156/521 |
| 3,534,953 | 10/1970 | Appleby | 156/443 X |
| 3,642,001 | 2/1972 | Sabee | 128/287 |
| 3,673,019 | 6/1972 | Erekson | 156/66 |
| 3,688,771 | 9/1972 | Werner | 156/289 X |

FOREIGN PATENTS OR APPLICATIONS

| | | |
|---|---|---|
| 805,481 | 12/1958 | United Kingdom |
| 1,195,724 | 6/1970 | United Kingdom |

*Primary Examiner*—William A. Powell
*Assistant Examiner*—David A. Simmons
*Attorney, Agent, or Firm*—Alexander, Sell, Steldt & DeLaHunt

[57] ABSTRACT

An apparatus and method for applying folded lengths of pressure-sensitive adhesive tape to articles with one-half of the adhesive surface of the tape length secured to an article and a liner secured to the other half of the adhesive surface. The adhesive tape is folded to leave the adhesive surface exposed. A liner which may be wider than the folded tape is then secured to the adhesive on one-half of the folded tape. The tape and liner composite is cut and a movable vacuum pad applies the cut length to the article with the exposed adhesive applied to the article. The wide liner is easily removed when the tape tab is to be used.

5 Claims, 7 Drawing Figures

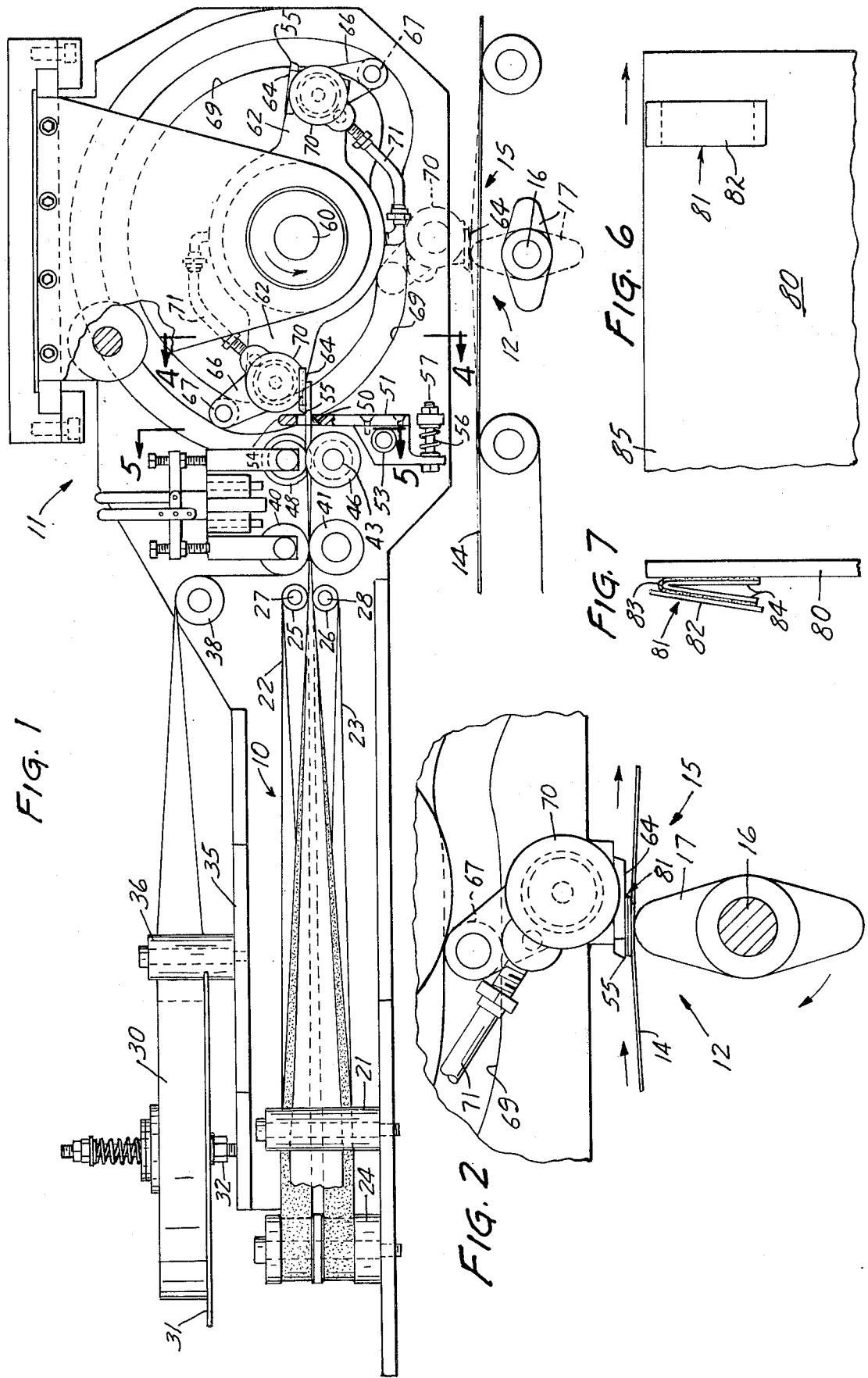

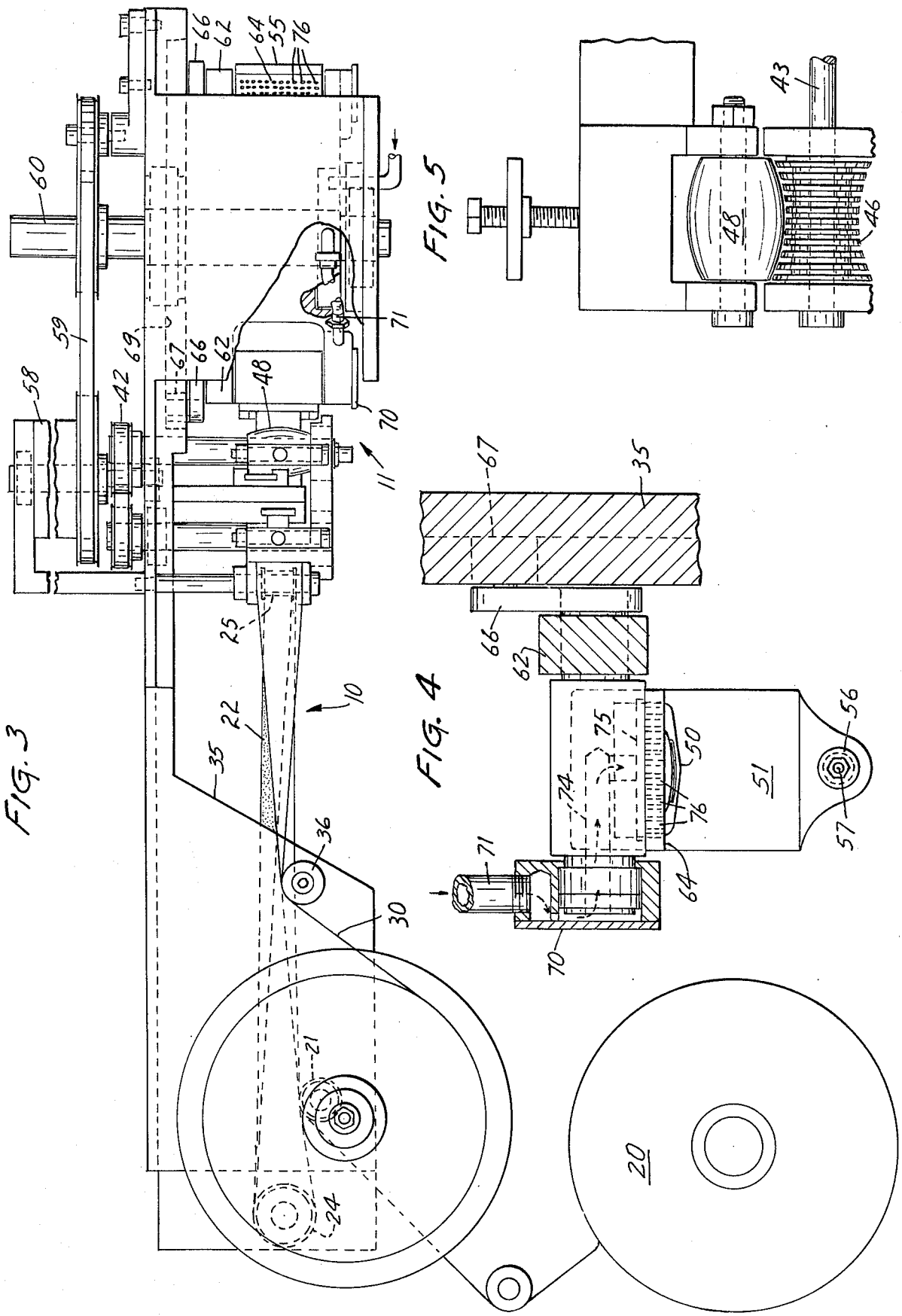

APPLICATOR FOR PRESSURE-SENSITIVE ADHESIVE FASTENERS

BACKGROUND OF THE INVENTION

This invention relates to an improved applicator for short lengths of adhesive tape to place the same on moving articles. One aspect of the invention is the apparatus for folding the pressure-sensitive adhesive tape upon itself to expose the adhesive coated surface, applying a liner to one surface of the folded adhesive tape, and applying cut lengths of the tape and liner composite to articles. Application of the cut lengths to the articles is handled by the use of a rotatable vacuum pad positioned and supported adjacent to a severing bar and which pad is rotated to cut a section of tape and carry the severed section into contact with the surface of a moving article, thus affording improved tape control.

Prior tape dispensing devices have utilized fixed guides or opposed rollers to fold a tape or to place a bow or bend in the tape. These devices have been utilized to place the pressure-sensitive tape around the edge of a sheet to reinforce the edge or have placed a bend or bow in the tape to give it rigidity such that a short length of tape could be extended outwardly beyond a supporting surface.

Prior art devices have also been available for cutting short lengths of tape and placing the same on a vacuum pad which will move the severed lengths of tape from the cutting member down into engagement with an article. Pad applicating devices which support a length of tape and place the same onto an article are well known, and one is illustrated in U.S. Pat. No. 3,472,724. In this device the pad is reciprocated to place the length of tape on an article which has been moved to the tape applying position and stopped. Other applicators for short lengths of tape are shown in U.S. Pat. No. 2,990,081 and 2,543,004.

The tape applicator of the present invention is adapted for placing tape fasteners to articles such as diapers, dental towels, aprons, bibs, etc., or lengths of tape to any article passed beneath the applying station. The fastener comprises a piece of pressure-sensitive adhesive tape with the backing folded upon itself and the adhesive coated surface exposed. A liner is laminated to an exposed surface of the pressure-sensitive tape and the other is adhered to the article such that when the liner is removed the tape may be unfolded to place the other pressure-sensitive adhesive surface into contact with another portion of the article.

The applicator comprises a novel tape folding apparatus utilizing a pair of endless webs having a roughened surface against which the pressure-sensitive adhesive tape may be applied and the belts are then directed along a path to place the roughened surfaces in opposed relation, thus causing the tape to be folded with the backing folded upon itself. A liner is applied to one adhesive surface of the folded tape and then the laminated tape and liner is directed across a cutting edge or blade. The tape is cut at the cutting edge by a rotating cutter bar whch is positioned adjacent to a pad upon which the cut lengths of laminate tape and liner are held. As the tape is cut the cut portion is held to the pad i.e., by differential air pressure and the same is carried by the rotating pad into contact with an article moving along a conveyor path. The pad is positioned to move along the path at a speed matching the conveyor and is brought into contact with a moving article moved along by the conveyor.

The applicator of the present invention utilizes a new method of applying tape fasteners in that the tape is first folded with the adhesive surface exposed, a liner having a width corresponding to or wider than one exposed surface of the adhesive tape is applied to that adhesive surface. The tape and liner laminate is then severed into predetermined lengths and the severed sections of tape and liner are moved into contact with an article to which the fastener is to be attached.

DESCRIPTION OF THE DRAWINGS

In the drawings:

FIG. 1 is an elevational view of an applicator of the present invention;

FIG. 2 is a detailed elevational view of the applicating station showing the tape support pad;

FIG. 3 is a plan view of the applicator of FIG. 1;

FIG. 4 is a sectional view taken along the line 4—4 of FIG. 1;

FIG. 5 is a detailed view taken along line 5—5 of FIG. 1;

FIG. 6 is a plan view of an article and a tape fastener according to the present invention; and FIG. 7 is an end view of the article and fastener of FIG. 6.

The machine of this invention is designed to fold lengthwise a strip of pressure-sensitive adhesive tape with the adhesive coated surface of the tape exposed after the backing has been folded upon itself. A releasable liner is laminated to the exposed pressure-sensitive adhesive on one surface of the folded tape. The laminate of the folded tape with the liner is then fed through sets of rollers and across a cutting edge. A cutting bar formed adjacent to a vacuum transfer pad cooperates with the cutting edge across which the laminate is fed to cut the laminate and transfer the cut strip of tape down to an applying station. The pad supporting the severed section of the tape moves the tape along the path of a conveyor which will move an article to which the tape is to be applied through the applying station. At the applying station the portion of the folded tape which is not laminated to the liner is pressed against the article and is separated from the applicating pad.

Referring now to the drawing there is shown in FIG. 1 an applicator constructed according to the present invention comprising a tape folding device generally designated by the reference numeral 10, a tape cutting and applying apparatus generally designated 11, and an article conveyor fragmentarily illustrated and indicated by the reference numeral 12. The conveying apparatus moves a strip of material 14 along a predetermined path through an applicating station 15. At the station 15, as illustrated, a driven shaft 16 rotates cam members 17 which raise areas of the article 14 successively out of the normal path of the article into contact with a pad for transferring a severed section of adhesive tape and liner laminate to the article. The article and the tape pad may alternatively follow paths that interfere.

The tape folding device 10 is adapted for folding a strip of pressure-sensitive adhesive tape 20, which tape comprises a backing having a pressure-sensitive adhesive coated on one surface. The pressure-sensitive adhesive tape 20 is drawn from a supply around a guide roller 21. As the tape 20 passes about the periphery of the roller 21 the pressure-sensitive adhesive surface is placed in contact with the roughened or irregular surfaces of two webs 22 and 23. The webs 22 and 23 are preferably endless belts formed on a flexible backing upon one surface of which is adhered a coating of abrasive particles. A preferred belt is available from Minnesota Mining and Manufacturing Company of St. Paul, Minnesota, U.S.A., and is sold as "Tri-M-ite" cloth coated abrasive 180X closed coat belts. This belt contains aluminum oxide abrasive material of 180 grit. A two ply endless woven cotton belt which is impregnated with neoprene might also be used as it has an irregular contoured surface and would release the adhesive. The weave provides a rough surface as contrasted to untextured neoprene belts. The belts 22 and 23 are supported at one end by a vertically disposed roller 24. The roller 24 is suitably journaled on a shaft and formed with enlarged shouldered portions at axially spaced ends to serve as guides for the belts passing around the roller. Alternatively, a pair of rollers may be supported on a pin in axially aligned relationship to support one end of each of the belts 22 and 23. The opposite ends of the belts 22 and 23 are supported by a set of rollers 25 and 26 positioned with their axis in parallel relationship. The axis of the rollers are aligned in the vertical direction and are spaced such that a nip is formed between the rollers and such that the belts 22 and 23 can pass therebetween plus the thickness of an adhesive tape which has been folded back upon itself. The belts 22 and 23 are so disposed that between the roller 24 and the pair of rollers 25 and 26 each belt is twisted 90°. Thus as shown in FIGS. 1 and 2, as the pressure-sensitive adhesive surface of the tape 20 is drawn around the roller 21 it is placed into contact with the roughened surface of each of the belts 22 and 23. The tape is then drawn between the nip of rollers 25 and 26 but the adhesive surface remains in contact with the roughened surface of the belts 22 and 23. Thus, as the tape travels toward the rollers 25 and 26 the same is folded. Rollers 25 and 26 are freely rotatably mounted on shafts 27 and 28. Movement of the pressure-sensitive adhesive tape 20 causes movement of the belts 22 and 23 and thus the pressure-sensitive adhesive tape is gradually folded upon itself as it is drawn between the rollers 25 and 26. The roller 24 could be driven or rollers 25 and 26 could be driven to advance the tape and the belts 22 and 23 to place a fold in the tape 20.

A liner stock 30 is advanced from a supply roll supported on a rotatable disk 31 which disk is supported by a shaft 32 from a main frame 35 of the apparatus. This supply of liner stock is drawn around a guide roller 36 and it in turn is rotated 90° to move around a second guide roller 38. The liner stock is then brought into contact with one surface of the folded pressure-sensitive adhesive tape 20 as the liner 30 and folded tape 20 are drawn between the nip of a laminating roller 40 and a driven roller 41. The roller 41 has a knurled surface and is driven by a belt 42 surrounding a pulley on a drive shaft to the roller 41. The belt 42 also drives a pulley associated with the shaft 43 of a second spool shaped roller 46 which is knurled and serves to place a bow in the laminated tape and liner.

Cooperating with the spool shaped roller 46 is a barrel shaped roller 48 which is adjustably mounted with respect to the spool to place a suitable bow in the laminated tape and liner so that it will extend rigidly from the nip between the rollers to permit the same to be pushed across the cutting edge 50 of a cutter member 51. The cutter member 51 comprises a plate 54 with a hole therethrough, one edge of which is beveled to form the cutting edge 50, and a block, which block is pivotally supported about a shaft 53. The plate 54 extends upwardly above the cutting edge 50 to be contacted by a cutting bar 55, insuring that the length of tape extending across the cutting edge 50 will be cut. The cutter member 51 is spring biased by a spring 56 against a stop, formed by a bolt 57 extending through a bracket and one leg on the block of the cutter member 51, to a position affording interference between the cutting edge 50 and the cutting bar 55 to be hereinafter described.

The drive for the rollers 41 and 46 is controlled by an electric clutch 58 which controls the transfer of power from a belt 59 to a drive shaft and drive pulley for driving the belt 42. The belt 59 is driven from a power input shaft 60 which may be driven with the conveyor equipment driving the articles along the conveyor path 14. The drive for the articles and the shaft 16 is such that shaft 60 and shaft 16 are sequentially operated and timed in accordance with the movement of the article 14. The feed of the tape 20 by the rollers 41 and 46 is further timed with the rotation of the shaft 60 to place a length of tape on the article at the proper interval.

Secured to the shaft 60 is a rotating member 62 having a pair of radially extending bifurcated arms which support pivotally a pair of tape applying pads 64. The pads 64 are pivotally mounted by trunnions which have one end journaled in one bifurcation of an arm on the member 62 and which extend through the bifurcation. One end of each trunnion is secured to a crank arm 66 to which crank arm is secured a cam follower 67 in the form of a roller. The cam follower 67 follows a continuous arcuate recessed cam track 69 provided in the frame 35 of the applicator. The opposite end of the trunnions supporting the pads 64 is movably mounted in the other bifurcation of the arm defining a housing 70 forming a manifold which manifold is connected to a conduit 71. The pair of conduits 71 is connected to a source of subatmospheric pressure such that a vacuum is drawn at the surface of each pad 64 through a passageway 74 formed in the trunnion and leading to a rectangular recess 75 over which a plate forming the pad 64 is secured. Each pad 64 is provided with a plurality of tiny openings 76 which communicate with the recess 75 and communicate with the surface of the pad such that a cut section of tape placed against the pad will be held thereon by the subatmospheric pressure created behind the tape. The pad 64 is a generally planar rectangular block secured to the trunnion to cover the recess 75 and abuts the cutter bar 55. The cutter bar 55 is positioned in relationship to the crank arm 66 such that the cutter bar 55 will cooperate with the cutting edge 50. As an alternative a separate cutting bar could be secured adjacent the pad on the trunnion.

The cam follower 67 and the cam 69 cooperate to position the pad 64 with the cutting bar 55 in a position to abut the guides 54 on the cutter member 51. After the cutting operation of the extended length of the liner 30 and the pressure sensitive adhesive tape 20 and pad 64 carries the severed section of tape down to the applicating station at which position the cam follower 67 and the cam track 69 is such that the pad 64 is positioned in a plane parallel to that of the path of the moving article. The pad moves in its path at a speed corresponding to that of the article 14, and when it is in a position above the shaft 16 the cam members 17 will force the article upward into engagement with the cut strip of tape held by the pad to effect a transfer from the pad to the article 14. Simultaneously, the subatmospheric pressure through the manifold in housing 70 could be interrupted so the release would not depend entirely on the strength of the adhesive at the time of the transfer.

The source of subatmospheric pressure is applied to the moving conduits 71 through a manifold fixed about the shaft 60 and having a sliding seal with the member 62 to which the conduits 71 are connected.

The number of pads disposed on the rotating member 62 depend on the number of applications of tape required and the interval of the applications. It is possible to have between one and four pads.

The article 14 to which the tape tabs are applied may subsequently be cut into rectangular sections. As identified in FIGS. 6 and 7, these sections may be in the form of a dental towel 80 which has a tape fastener 81 adhered thereto. The fastener comprises the liner 82 releasably adhered to the exposed adhesive 83 of the tape which includes the backing 84. The liner 82 may be released and the towel wrapped around the patient and the corner 85 secured by the fastener 81 by straightening the tape backing 84.

Having thus described the invention, it is to be understood that modifications may be made without departing from the spirit of the invention as defined in the appended claims.

What is claimed is:

1. An applicator for cutting lengths of pressure-sensitive adhesive tape and applying the same to an article moving along a first path, said applicator comprising:
    means for feeding a length of said tape along a second path,
    a cutting edge disposed on one side of said second path,
    vacuum pad means for supporting a severed length of tape, said vacuum pad means comprising a generally rectangular pad,
    cutting means movable with said pad means and cooperating with said cutting edge to sever a length of said tape,
    mounting means for supporting said vacuum pad means and said cutting means for movement relative to said cutting edge and for moving said pad means along a third orbital path around an axis past said cutting edge to place the severed lengths of said tape on said pad means and for orienting said pad means to a position generally parallel to and along said first path to apply said severed length of tape to a said article, said mounting means comprising a rotating arm movably supporting said pad means, means for rotating said arm about said axis, and cam means for orientating said pad means during rotation of said arm and for defining said third orbital path, and
    wherein said cutting means is mounted on said arm to move with said pad means and to cooperate with said cutting edge to cut sections from said tape.

2. An applicator according to claim 1 wherein said arm supports a pair of vacuum pad means, one on generally diametrically opposite sides of said axis from the other.

3. An applicator for cutting lengths of pressure-sensitive adhesive tape and applying the same to an article moving along a first path, said applicator comprising:
    means for feeding a length of said tape along a second path,
    a cutting edge disposed on one side of said second path,
    vacuum pad means for supporting a severed length of tape, said vacuum pad means comprising a plurality of perforated plate members supported in circumferentially spaced positions on a rotating member,
    cutting means movable with said pad means and cooperating with said cutting edge to sever a length of said tape,
    mounting means for supporting said vacuum pad means and said cutting means for movement relative to said cutting edge and for moving said pad means along a third orbital path around an axis past said cutting edge to place the severed lengths of said tape on said pad means and for orienting said pad means to a position generally parallel to and along said first path to apply said severed length of tape to a said article, said mounting means comprising a cam track followed by a cam fixed to each of said plate members to move said plate members in relation to said rotating member to orient said plate members.

4. An applicator for cutting lengths of folded pressure-sensitive adhesive tape to one surface of which has been applied a release liner and applying the exposed adhesive surface of the cut lengths of tape to an article moving along a first path, said applicator comprising:
    means for feeding a length of said tape along a second path,
    means for folding said length of tape upon itself with the adhesive coated surface exposed,
    means for laminating a release liner to the adhesive on one side of the folded tape,
    feed means for advancing said laminated tape and liner along a third path,
    a resiliently biased cutting blade disposed along said third path,
    vacuum pad means for supporting a severed length of said laminated tape and liner, said vacuum pad means comprising a generally rectangular pad having a support surface,
    cutting means cooperating with said resiliently biased blade to sever a length of said laminated tape and liner,
    mounting means for supporting said vacuum pad means and said cutting means for orbital movement along a fourth path around an axis past said blade to place the successive severed lengths of said laminated tape and liner on said support surface of said pad means and for orienting said pad means along said first path with said support surface positioned to apply said severed lengths of laminated tape and liner successively to a said article, said mounting means comprising a rotating arm movably supporting said pad means, means for rotating said arm about said axis, and cam means for orientating said pad means during rotation of said arm and for defining said fourth orbital path, and
    wherein said cutting means is mounted on said arm to move with said pad means and to cooperate with said cutting edge to cut lengths from said laminated tape and liner.

5. An applicator according to claim 4 wherein said arm supports a pair of vacuum pad means, one on generally diametrically opposite sides of said axis from the other.

* * * * *